United States Patent [19]

Hooven et al.

[11] Patent Number: 4,576,035

[45] Date of Patent: Mar. 18, 1986

[54] SELF-CALIBRATING DIFFERENTIAL CONDITION SENSOR

[75] Inventors: Michael D. Hooven; Stanley H. Saulson, both of Miami, Fla.

[73] Assignee: Cordis Corporation, Miami, Fla.

[21] Appl. No.: 763,891

[22] Filed: Aug. 9, 1985

Related U.S. Application Data

[63] Continuation of Ser. No. 568,537, Jan. 5, 1984, abandoned.

[51] Int. Cl.⁴ .................................. G01L 27/00
[52] U.S. Cl. .................... 73/4 R; 73/714; 73/756; 128/748; 364/558; 364/571
[58] Field of Search .............. 128/748; 364/558, 571; 137/571; 73/4 R, 756, 753, 714

[56] References Cited

U.S. PATENT DOCUMENTS

| 1,381,139 | 6/1921 | Smoot | 73/716 |
| 3,313,157 | 4/1967 | Gilson | 73/714 |
| 3,585,841 | 6/1971 | Brandau | 73/4 R |
| 4,339,943 | 7/1982 | Hedrick | 73/4 R |
| 4,384,925 | 5/1983 | Stetter et al. | 364/571 |

Primary Examiner—Donald O. Woodiel
Attorney, Agent, or Firm—George H. Gerstman

[57] ABSTRACT

A self calibrating differential pressure sensor having a pair of pressure transducers connected in fluid series with two on/off valves. The system can be calibrated to eliminate base line or zero shift and can also be used to measure other variable conditions, such as differential voltage between two voltage points or differential chemical concentrations between two concentration points.

8 Claims, 2 Drawing Figures

SELF-CALIBRATING DIFFERENTIAL CONDITION SENSOR

This application is a continuation of U.S. application Ser. No. 568,537, filed Jan. 5, 1984, now abandoned.

BACKGROUND OF THE INVENTION

This invention relates in general to measurement systems and, in particular, to a self calibrating differential sensor for measuring pressure, chemical, electrical and other conditions.

More specifically, but without restriction to the particular use which is shown and described, this invention relates to a self calibrating differential sensor, such as for use in the measurement of pressure differential, temperature differential, differential chemical parameters and other physical parameters. The system of the invention is independent of base line or zero shift.

In the measurement of many conditions, the measuring device is subject to error due to shift of the base line of the calibration for the measurement. The introduction of such error may result from changes in numerous environmental or physical factors. This calibration problem is often encountered in pressure transducers in which a base line shift can occur in response to variations in temperature, barometric pressure, reference pressure, packaging stresses, deterioration of electronic components, and a variety of other causes. Such shifts are a major problem in fully implantable pressure transducers for living bodies where long-term biomedical applications are intended for five years or longer. Known devices require periodic calibration in order to maintain acceptable transducer accuracy, generally $E_{max} = \pm 15$ mm $H_2O$. This calibration procedure normally requires some type of invasive surgical procedure, such as, for example, lumbar puncture. It is generally accepted that base line shift is a major cause of transducer inaccuracy in body implantable applications.

SUMMARY OF THE INVENTION

It is therefore an object of this invention to provide a self calibrating differential condition sensor.

Another object of this invention is to provide a differential sensor for pressure or other physical conditions capable of being automatically zero calibrated.

A further object of the invention is to provide a differential measuring system which is unaffected by environmental changes and the like.

These and other objects are attained in accordance with the present invention wherein there is provided a self calibrating differential sensor for measuring pressure, temperature, chemical concentrations, and the like. Although the system has equally important applications to the measurement of chemical conditions, such as chemical concentrations, electrical conditions, such as voltage differences, and other parameters, the invention is described with reference to a differential pressure sensor. The pressure sensor system may include two absolute pressure transducers in fluid communication with two fluid controls valves. The valves are selectively opened or closed for purposes of calibration and differential measurement. The invention of the application is unaffected by base line or zero shift, such as caused by changes in temperature, parameter barometric pressure, and the like.

The system is ideally suited for use with a fully implantable pressure sensor for long-term biomedical use, where base line shift over time is a particular problem.

DESCRIPTION OF THE DRAWINGS

Further objects of the invention, together with additional features contributing thereto and advantages accruing therefrom, will be apparent from the following description of preferred embodiments of the invention, which are shown in the accompanying drawings with like reference numerals indicating corresponding parts throughout, wherein.

DESCRIPTION OF THE PREFERRED EMBODIMENTS

Figure 1:
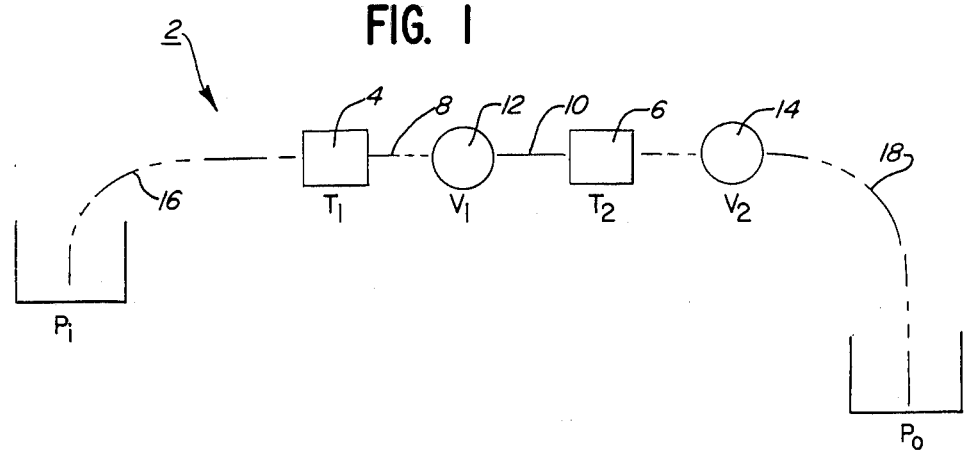
FIG. 1 is a schematic diagram of a self calibrating differential pressure sensor of the invention.

Referring now to FIG. 1, there is illustrated a schematic diagram of self calibrating, differential pressure sensor of the invention, generally designated by reference numeral 2. Although the invention is described with reference to the measure of a pressure differential namely ($P_i$, $P_o$), the teachings of the application can be used to measure numerous other physical parameters, such as, for example, differential voltage between two voltage points, differential chemical concentrations between two concentration points, and numerous other conditions by employing in the system suitable sensor and transducers responsive to such conditions.

In FIG. 1, the system is shown having a pair of absolute pressure transducers 4 and 6 ($T_1$, $T_2$) in liquid communication in series through suitable fluid lines 8, 10, with a pair of on/off valves 12, 14 ($V_1$, $V_2$). The transducers 4 and 6 ($T_1$, $T_2$) measure absolute pressure, and valves 12 and 14 ($V_1$, $V_2$) can either be open or closed to flow. The pressure transducer 4 ($T_1$) is in fluid communication with an input pressure ($P_i$) through a fluid line 16 as shown, and valve 14 ($V_2$) is connected to an output pressure ($P_o$) by line 18.

From FIG. 1, it should be apparent that when valve 12 ($V_1$) is closed, and valve 14 ($V_2$) is open, the pressure transducer 4 ($T_1$) measures the pressure $P_i$ while transducer 6 ($T_2$) measures the pressure $P_o$. With valve 14 closed and valve 12 open, both transducers 4 and 6 measure pressure $P_i$. With valves 12 and 14 open, it should be clear that an open fluid communication between pressures $P_i$ and $P_o$ exists.

The sensor of the invention can be used to measure differential pressure ($P_i - P_o$) with valve 12 ($V_1$) closed and valve 14 ($V_2$) open. The device can also be used as a flow meter if both valves 12 and 14 are open, and if a known restriction exists between the transducers 4 and 6. The transducers can also be other than pressure devices and be chemical, electrical or other sensors to measure differential electrical, chemical and such conditions. It is within the scope of the invention to eliminate valve 14, if the differential pressure across valve 12 is small with valves 12 and 14 open. This will be clear from the following description of the calibration procedures of the instrument.

Figure 2:
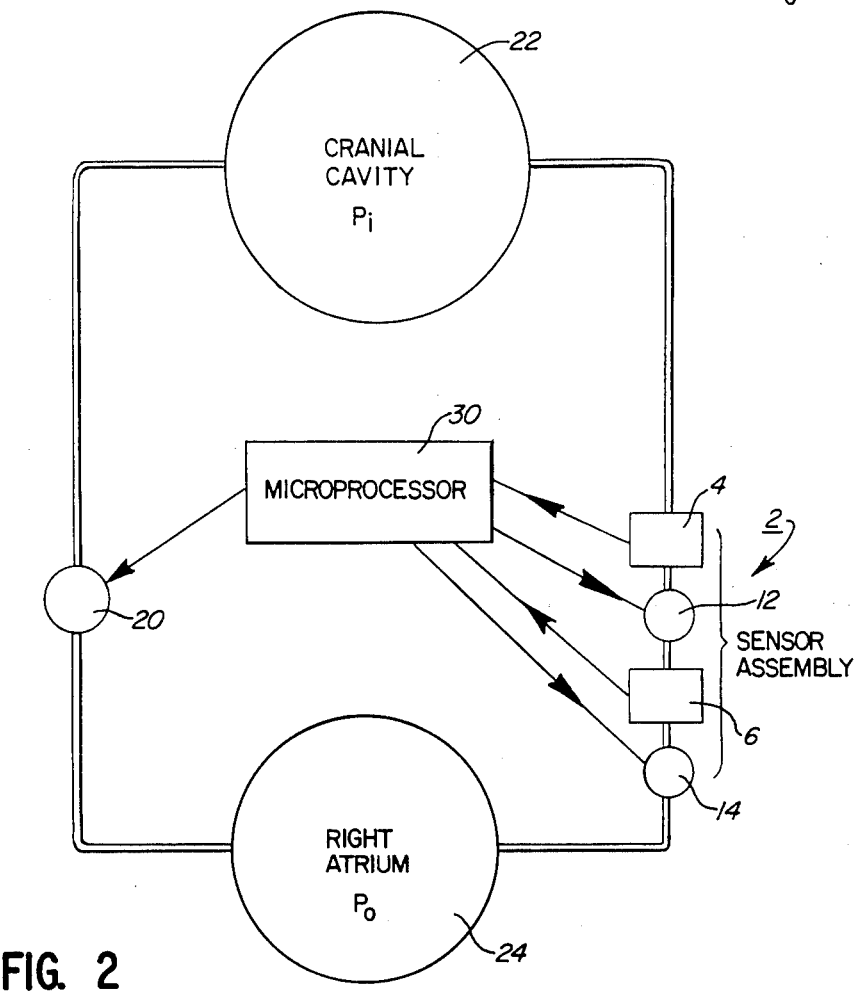
FIG. 2 is a schematic diagram of an implantable pressure monitoring system utilizing the principles of the invention.

Referring now to FIG. 2, there is illustrated an example of a use of the self calibrating sensor 2 of the invention, as previously described. The system 2 is ideally suited to a fully implantable pressure monitoring system, such as a "closed loop" system, as proposed by National Aeronautics and Space Administration.

In FIG. 2, an embodiment of the sensor 2 of the invention employed in such an application is shown, although it is possible to use the system to accomplish such results in other applications. In FIG. 2, the sensor 2 is used as a feedback control for a pump or valve system 20 designated to maintain a constant pressure differential of the fluid between the cranial cavity 22 and the right atrium 24 of the heart. The output of the transducers, such as transducers 4 and 6 in FIG. 1, are transmitted to a microprocessor 30, as shown in FIG. 2. The microprocessor 30, in turn, then is connected to the control valves ($V_1$, $V_2$), such as valves 12 and 14 in FIG. 1, and control the zero reading to calibrate the system. Corrected pressure readings are employed to control the pump or valve system 20 through the microprocessor 30 to supply or drain fluid to and from the cranial cavity 22 and maintain the desired pressure differential. The sensor is ideally suited for such uses, because reliable pressure readings can be achieved without referencing atmospheric or any known pressure.

The system 2, as shown in FIG. 1, may be calibrated through the following calibration procedure. In the following explanation, $V_1$ and $V_2$ respectively refer to valves 12 and 14, while $T_1$ and $T_2$ are equivalent to pressure transducers 4 and 6.

CALIBRATION PROCEDURE

Valve $V_2$ is shut and $V_1$ open as shown, so that both transducers read $P_i$.

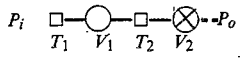

$P_{T1}(P_i)$ = output from transducer $T_1$ at pressure $P_i$
$P_{T2}(P_i)$ = output from transducer $T_2$ at pressure $P_i$
The error at $P_i$ is simply:

$$E(P_i) = P_{T1}(P_i) - P_{T2}(P_i)$$

If we assume that $E(P_i)$ is due to base line shift, then:

$$E(P_i) = \text{const} = E$$

To measure the *corrected* differential pressure, close $V_1$ and open $V_2$:

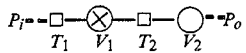

Transducers outputs are $P_{T1}(P_i)$ and $P_{T2}(P_o)$

The *corrected* differential pressure is then:

$$\Delta P = P_i - P_o$$

$$= \underbrace{\frac{P_{T1}(P_i) - P_{T2}(P_o)}{1}}_{\text{uncorrected } P} - \underbrace{\frac{E}{1}}_{\substack{\text{correction for} \\ \text{base line shift}}}$$

Using the calibration procedure to determine the base line shift error E, we can therefore correct the transducer readings to result in an accurate measurement of $\Delta P$. If $\Delta P = P_{T1}(P_i) - P_{T2}(P_o) - E$ is small (O) with $V_1$ open, then $V_2$ can be eliminated, and the system can be calibrated as described with $V_1$ open.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A method for calibrating a differential physical condition measurement, which comprises the steps of:
   coupling, to a first element having a first variable physical condition, a first sensing device adapted to detect the magnitude of said first condition;
   coupling, to said first element, a first valve and a second sensing device adapted to detect the magnitude of said first condition when said first valve is open, said second sensing device being operable independent of said first sensing device;
   coupling, between a second element having a second variable physical condition and said second sensing device, a second valve whereby said second sensing device is adapted to detect the magnitude of said second condition when said second valve is open;
   controlling said first valve and said second valve to (a) open said first valve and close said second valve whereby said first sensing device and said second sensing device both sense said first variable physical condition to obtain an error factor, and (b) close said first valve and open said second valve whereby said first sensing device senses said first variable physical condition and said second sensing device senses said second variable physical condition in order to obtain a condition difference amount; and
   algebraically subtracting said error factor from said condition difference amount to obtain a corrected differential condition amount.

2. A method as described in claim 1, and further including the steps of:
   providing a device for maintaining a desired physical condition differential; and
   controlling said maintaining device in response to the corrected differential condition amount.

3. A method as described in claim 1, wherein said physical condition is pressure and said sensor devices are pressure transducers.

4. A method for controlling a pressure differential which comprises the steps of:
   coupling, to a first element having a first variable pressure, a first pressure transducer adapted to detect the magnitude of said first pressure;
   coupling, to said first element, a first valve and a second pressure transducer adapted to detect the magnitude of said first pressure when the first valve is open, said second pressure transducer being operable independent of said first pressure transducer;
   coupling, between a second element having a second variable pressure and said second pressure transducer, a second valve whereby said second pressure transducer is adapted to detect the magnitude of said second pressure when the second valve is open;

controlling said first valve and said second valve to (a) open said first valve and close said second valve whereby said first pressure transducer and said second pressure transducer both sense said first pressure to obtain an error factor, and (b) close said first valve and open said second valve whereby said first pressure transducer senses said first pressure and said second pressure transducer senses said second pressure in order to obtain a pressure difference;

algebraically subtracting said error factor from said pressure difference to obtain a corrected differential pressure;

providing a pump or valve for maintaining a desired pressure differential; and controlling said pump or valve in response to the corrected differential condition.

5. A method as described in claim 4, in which said first element comprises one of the cranial cavity and another body chamber and said second element comprises the other one of the cranial cavity and said other body chamber.

6. Apparatus for calibrating a differential physical condition measurement, comprising:

first sensor means coupled to a first variable physical condition element and adapted to detect the magnitude of said first condition;

second sensor means coupled to said first variable physical condition element through a first valve and to a second variable physical condition through a second valve;

said second sensor means being operable independent of said first sensor means;

means controlling said first valve and said second valve to (a) open said first valve and close said second valve whereby said first sensor means and said second sensor means both sense said first variable physical condition to obtain an error factor, and (b) close said first valve and open said second valve whereby said first sensor means senses said first variable physical condition and said second sensor means senses said second variable physical condition in order to obtain a condition difference amount; and means for aLgebraically subtracting said error factor from said condition difference amount to obtain a corrected differential condition amount.

7. Apparatus as described in claim 6, and further including:

means for maintaining a desired physical condition differential; and means for controlling said maintaining device in response to the corrected differential condition amount.

8. Apparatus as described in claim 6, in which said physical conditions comprise pressure and said sensor means comprise pressure transducers.

* * * * *